(12) United States Patent
Horii

(10) Patent No.: US 8,716,008 B2
(45) Date of Patent: May 6, 2014

(54) DETECTION METHOD AND DETECTION SYSTEM

(75) Inventor: Kazuyoshi Horii, Kanagawa-ken (JP)

(73) Assignee: Fujifilm Corporation, Tokyo (JP)

( * ) Notice: Subject to any disclaimer, the term of this patent is extended or adjusted under 35 U.S.C. 154(b) by 540 days.

(21) Appl. No.: 12/906,797

(22) Filed: Oct. 18, 2010

(65) Prior Publication Data

US 2012/0094397 A1   Apr. 19, 2012

(51) Int. Cl.
*C12M 1/34* (2006.01)

(52) U.S. Cl.
USPC ..................................... 435/288.5; 422/417

(58) Field of Classification Search
None
See application file for complete search history.

(56) References Cited

U.S. PATENT DOCUMENTS

| | | | |
|---|---|---|---|
| 6,194,223 | B1 | 2/2001 | Herrmann et al. |
| 2001/0027918 | A1* | 10/2001 | Parce et al. ............... 204/452 |
| 2004/0253744 | A1* | 12/2004 | Rife et al. ................. 436/514 |
| 2005/0053974 | A1 | 3/2005 | Lakowicz et al. |
| 2009/0162944 | A1 | 6/2009 | Kase et al. |

FOREIGN PATENT DOCUMENTS

| | | |
|---|---|---|
| JP | 10-307141 A | 11/1998 |
| JP | 2007-101221 A | 4/2007 |
| WO | WO 2004/104584 A1 | 2/2004 |

OTHER PUBLICATIONS

M.M.L.M. Vareiro et al., "Surface Plasmon Fluorescence Measurements of Human Chorionic Gonadotrophin: Role of Antibody Orientation in Obtaining Enhanced Sensitivity and Limit of Detection", Analytical Chemistry, vol. 77, pp. 2426-2431, 2005.
T. Liebermann and W. Knoll, "Surface-plasmon field-enhanced fluorescence spectroscopy", Colloid and Surfaces, vol. A171, pp. 115-130, 2000.
K. Tsuboi, et al., "High-sensitivity sensing of catechol amines using by optical waveguide mode enhanced fluorescence spectroscopy", Preprints for the Spring Meeting 2007 of the Japan Society of Applied Physics, No. 3, p. 1378, 28p-SA-4.

* cited by examiner

*Primary Examiner* — Chris L Chin
(74) *Attorney, Agent, or Firm* — McGinn IP Law Group, PLLC

(57) ABSTRACT

In a detection method for detecting the quantity of a target material, a labeled binding material in the amount corresponding to the quantity of the target material contained in a liquid specimen is bonded to the top of a sensor portion; and a signal based on light emitted from a label in an evanescent field or an enhanced optical field produced on a surface of the sensor portion when the sensor portion is irradiated with excitation light is detected. After the labeled binding material is bonded to the immobilization layer, the signal is detected while the fluid over the sensor portion is controlled to flow at a constant flow rate at which bonds between the labeled binding material and the immobilization layer are not broken and the above signal can be detected with a greater magnitude than when the liquid specimen exists over the sensor portion at rest.

11 Claims, 8 Drawing Sheets

DISTRIBUTION OF FLOW RATE IN CHANNEL
(LAMINAR FLOW)

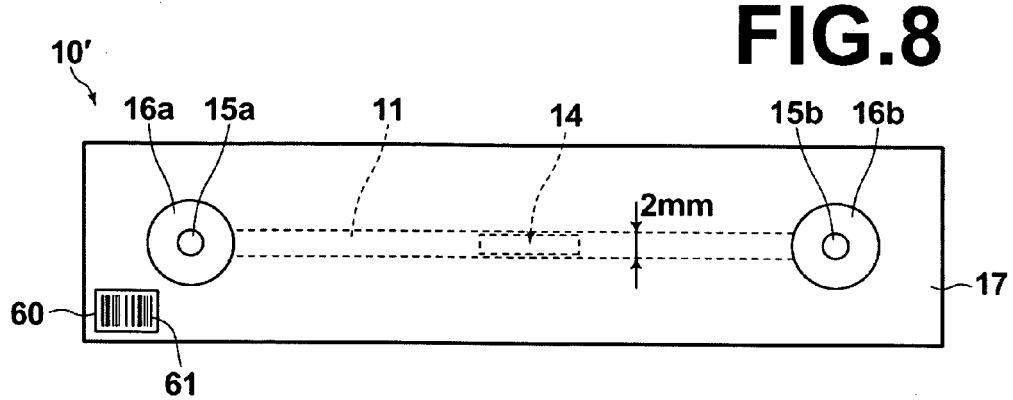
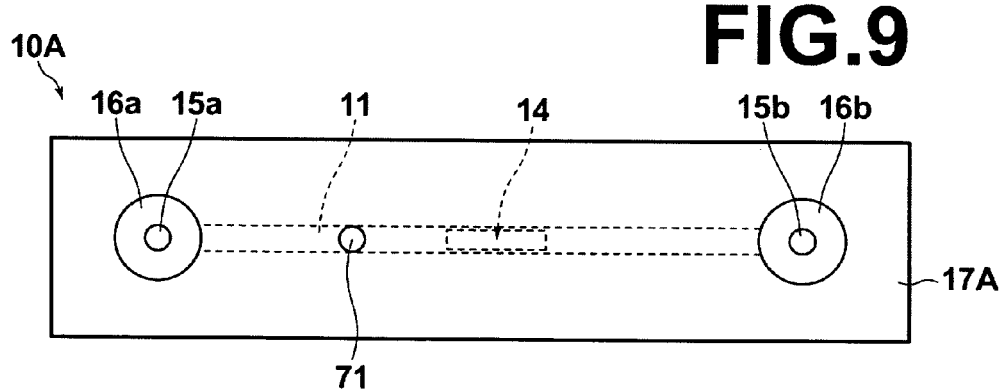
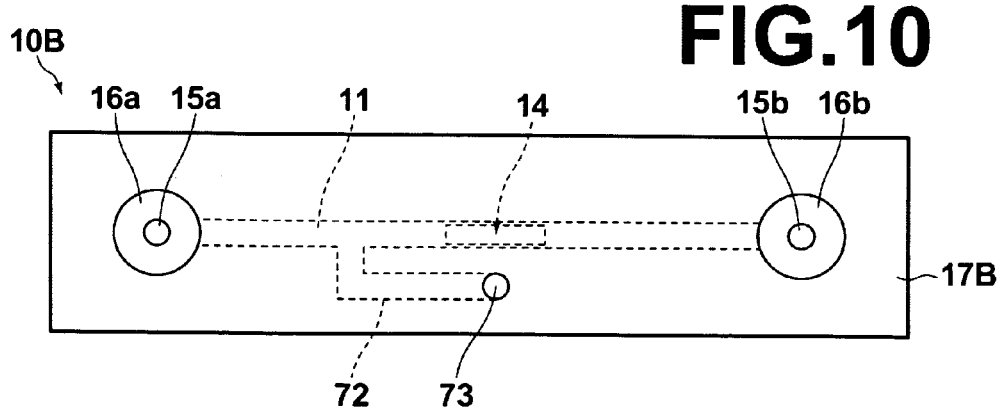

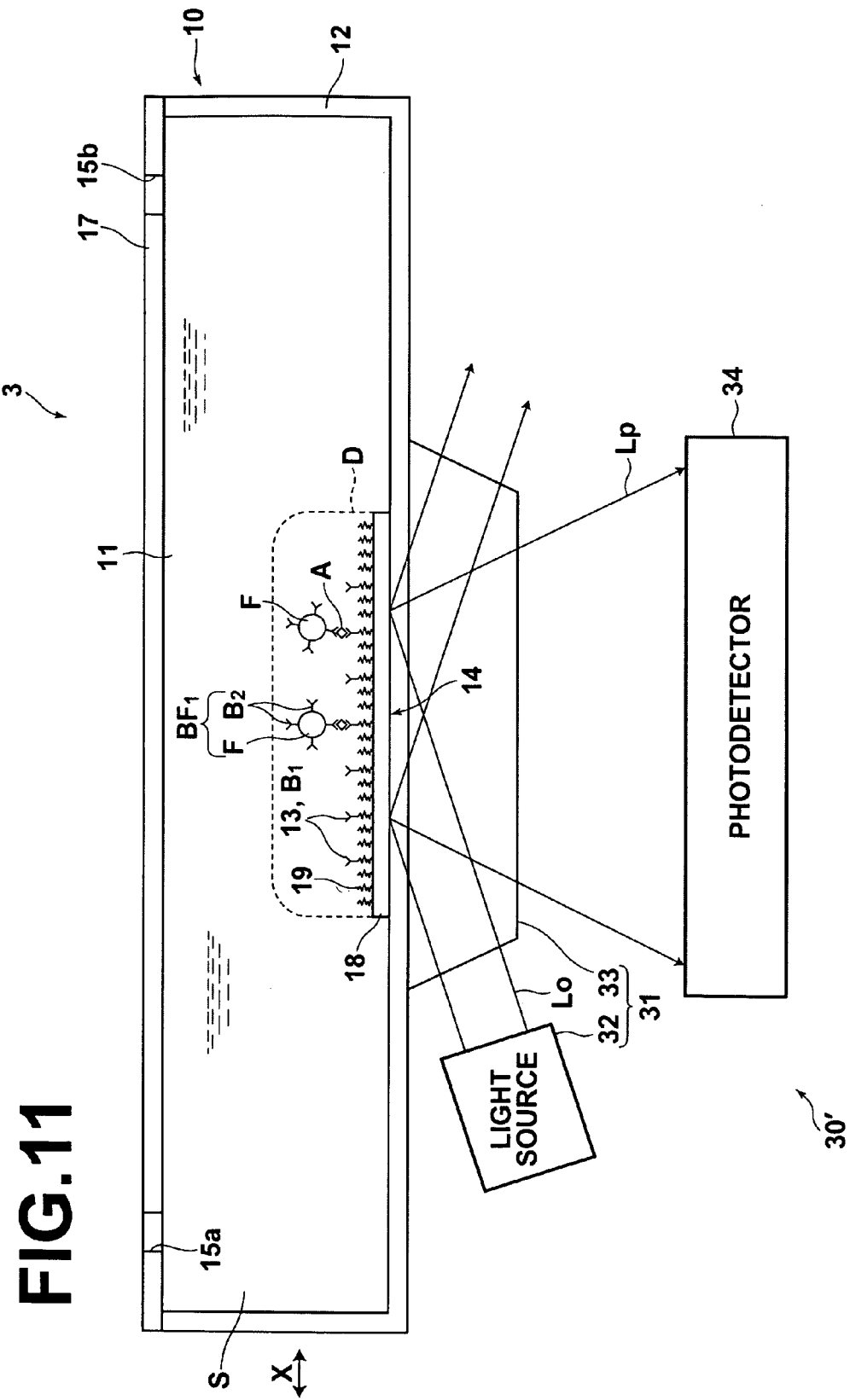

DETECTION METHOD AND DETECTION SYSTEM

BACKGROUND OF THE INVENTION

1. Field of the Invention

The present invention relates to a detection method and a detection system for detecting a target material (i.e., a material to be detected) in a specimen, and in particular, to a detection method and a detection system for detecting the target material by detection of an optical signal by use of an evanescent field or an enhanced optical field.

2. Description of the Related Art

Conventionally, fluorescence detection is widely used as a simple high-sensitivity measurement technique in the field of biomeasurement and the like. The fluorescence detection is a technique for confirming existence of a target material which emits fluorescence when excited by light at a specific wavelength, by irradiating with excitation light having the specific wavelength a specimen which is expected to contain the target material, and detecting the emitted fluorescence. In addition, according to another technique which is widely used in the case where the target material is not a fluorescent material, a material which is labeled with a fluorescent dye and can be specifically bonded to the target material is brought into contact with the specimen, and the existence of the target material or the specific bonding is confirmed by detecting fluorescence in a similar manner to the case where the target material is a fluorescent material.

In the field of biomeasurement, for example, in order to detect an antigen as a target material contained in a specimen, assays such as sandwich ELISA (Enzyme-linked Immunosorbent Assay) or competitive ELISA are performed. According to sandwich ELISA, a primary antibody which can be specifically bonded to the target material is immobilized on a substrate, and a specimen is supplied onto the substrate, so that the target material is specifically bonded to the primary antibody. Subsequently, a secondary antibody which is fluorescence labeled and can be specifically bonded to the target material is added so as to make the secondary antibody bonded to the target material. Thus, the so-called sandwich of the primary antibody, the target material, and the secondary antibody is formed. Then, fluorescence emitted from the fluorescence label of the secondary antibody is detected. According to competitive ELISA, a fluorescent-labeled secondary antibody which can be specifically bonded to a primary antibody in competition with a target material is put in competition with the target material for specific bonding to the primary antibody, and fluorescence emitted from the secondary antibody bonded to the primary antibody is detected.

In order to detect, in sandwich ELISA or competitive ELISA, the fluorescence which is emitted from the secondary antibody bonded through the target material to the primary antibody immobilized on the substrate, or from only the secondary antibody directly bonded to the primary antibody, the evanescent-excited fluorescence technique, in which fluorescence is excited by evanescent light, has been proposed. According to the evanescent-excited fluorescence technique, excitation light which is totally reflected at the front surface of a substrate is injected from the rear surface of the substrate, and fluorescence emitted by excitation by an evanescent wave leaking from the front surface of the substrate is detected.

In addition, techniques of utilizing an effect of plasmon resonance enhancing an electric field in order to increase the sensitivity in the evanescent-excited fluorescence technique have been proposed in the Patent Literature 1, the Non-patent Literature 1, and the like. In the surface plasmon-enhanced fluorescence technique, a metal layer is arranged on a substrate for causing plasmon resonance, and excitation light is injected from the rear surface of the substrate to the interface between the substrate and the metal layer at an angle equal to or greater than the total reflection angle so as to produce surface plasmons in the metal layer. Thus, the fluorescence signal is enhanced by the field enhancing effect of the surface plasmons, so that the S/N is increased.

Further, a technique of enhancing the electric field in a sensor portion by utilizing the field enhancing effect of the optical waveguide mode has been proposed in the Non-patent Literature 2. In the optical waveguide mode-enhanced fluorescence spectroscopy (OWF) proposed in the Non-patent Literature 2, a metal layer and an optical waveguide layer of a dielectric or the like are formed in this order on a substrate, and excitation light is injected from the rear surface of the substrate at an angle equal to or greater than the total reflection angle so as to cause an optical waveguide mode in the optical waveguide layer. Thus, the fluorescence signal is enhanced by the field enhancing effect of the optical waveguide mode.

Furthermore, according to the techniques proposed in the Patent Literature 2 and the Non-patent Literature 3, the fluorescence emitted from the fluorescent label which is excited by the electric field enhanced by surface plasmons is not detected, and instead the surface plasmon-coupled emission (SPCE) caused by surface plasmons newly induced in the metal film by the fluorescence is extracted from the prism side.

As mentioned above, in the field of biomeasurement, various techniques for detecting the target material have been proposed. According to the proposed techniques, the plasmon resonance or the optical waveguide mode is caused by irradiation with excitation light, the fluorescent label is excited by an electric field enhanced by the plasmon resonance or the optical waveguide mode, and the fluorescence is detected directly or indirectly.

The produced evanescent field and the enhanced electric field in the evanescent-excited fluorescence technique are known to rapidly damp with increase in the distance from the surface at which the electric field is produced. FIG. 12 is a graph indicating the dependence of the effect of surface plasmons enhancing an electric field on the distance from the surface (the metal surface) on which the enhanced electric field is produced. Specifically, FIG. 12 indicates a result of a simulation which has been performed for a system in which a solvent (water) exists on a sensor constituted by a prism (of polymethyl methacrylate (PMMA) resin) and a gold film having the thickness of 50 nanometers and being formed on the prism, under the condition that excitation light (having the laser wavelength of 656 nanometers) is injected onto the interface between the prism and the gold film at the incident angle of 72.5 degrees. It can be confirmed, from the graph of FIG. 12, that the degree of enhancement of the electric field is reduced by half at the distance of approximately 100 nanometers. Therefore, it is preferable that the fluorescence label be located close to the surface at which the enhanced electric field is produced.

On the other hand, in the field of biomeasurement, there is a demand for enabling measurement in a shorter time. Therefore, various techniques for efficiently causing reactions on the sensor portion and reducing the measurement time have been proposed. For example, a process being performed in a DNA chip and including a plurality of reaction stages has been proposed in the Patent Literature 3. In the process, a fluid is controlled so as to flow at a flow rate appropriate for each of stages in which the fluid is brought into contact with a functional substrate. Further, a technique for moving fluid in a microchannel at extremely high speed for measurement has been proposed in the Patent Literature 4.

[Patent Literature 1] Japanese Unexamined Patent Publication No. (1998)-307141
[Patent Literature 2] U.S. Patent Application Publication No. 20050053974
[Patent Literature 3] International Patent Publication No. WO2004/104584
[Patent Literature 4] Japanese Unexamined Patent Publication No. 2007-101221
[Non-patent Literature 1] M. M. L. M. Vareiro et al., "Surface Plasmon Fluorescence Measurements of Human Chorionic Gonadotrophin: Role pf Antibody Orientation in Obtaining Enhanced Sensitivity and Limit of Detection", Analytical Chemistry, Vol. 77, pp. 2426-2431, 2005
[Non-patent Literature 2] K. Tsuboi et al., "High-sensitive sensing of catechol amines using by optical waveguide mode enhanced fluorescence spectroscopy", Preprints for the Spring Meeting 2007 of the Japan Society of Applied Physics, No. 3, p. 1378, 28p-SA-4
[Non-patent Literature 3] T. Libermann and W. Knoll, "Surface-plasmon field-enhanced fluorescence spectroscopy", Colloid and Surfaces, Vol. A171, pp. 115-130, 2000

As explained above, in the case where an optical signal emitted from the vicinity of the sensor portion is detected by the evanescent evanescent-excited fluorescence technique, or the optical signal is detected after enhancing the optical field of the evanescent light by the plasmon resonance or the optical waveguide mode, the effect of enhancement by the plasmon resonance or the optical waveguide mode rapidly damps with increase in the distance from the surface of the metal layer or the optical waveguide layer. That is, even when the distance from the above surface to the fluorescent label increases by a small amount, the optical signal greatly damps. Therefore, the signal detection is required to be performed under the condition that the label is located as close as possible to the surface of the sensor portion.

SUMMARY OF THE INVENTION

The present invention has been made in view of the above circumstances.

The object of the present invention is to provide a detection method and a detection system which enable signal detection under the condition that the label is located close to the surface of the sensor portion.

The detection method according to the present invention includes the steps of: preparing a channel type sensor chip in which a sensor portion is arranged in a microchannel formed in a channel member, where a liquid specimen is to flow through the microchannel, and the sensor portion includes an immobilization layer capable of being bonded to a labeled binding material containing an attached label which emits light when irradiated with excitation light; bonding to the immobilization layer the labeled binding material in an amount corresponding to the amount of a target material contained in the liquid specimen, by making the liquid specimen flow through the microchannel; and detecting the quantity of the target material by detecting a signal based on light emitted from the label existing in an evanescent field or an enhanced optical field which is produced over a surface of the sensor portion when the sensor portion is irradiated with the excitation light.

The detection method according to the present invention is characterized in that, after the labeled binding material is bonded to the immobilization layer, the liquid specimen is controlled to flow at a constant flow rate at which bonds between the labeled binding material and the immobilization layer are not broken and the signal can be detected with a greater magnitude than when the liquid specimen exists over the sensor portion at rest, and the signal is detected while the liquid specimen flows at the constant flow rate.

That is, according to the present invention, the above signal is detected while the liquid specimen is controlled to flow at a constant flow rate so that a laminar flow is realized over the sensor portion.

The "labeled binding material" is a binding material which is labeled and can be bonded to the top of the sensor portion in the amount corresponding to the quantity of the target material. For example, in the case where sandwich ELISA is performed, the labeled binding material is composed of a binding material which can be specifically bonded to the target material, and a label. In the case where competitive ELISA is performed, the labeled binding material is composed of a binding material which can compete with the target material, and a label.

The label is not specifically limited as long as the label is optically responsive to the excitation light. For example, the label may be a fluorescent dye molecule, a fluorescent microparticle, or a quantum dot (semiconductor microparticle) which emits fluorescence in response to irradiation with excitation light, or a metal microparticle which scatters the excitation light.

The expression "detecting the quantity of the target material" includes detecting whether or not the target material exists.

The "enhanced optical field" is an enhanced electric field of light. The electric field of light (optical field) may be enhanced by either plasmon resonance or excitation of an optical waveguide mode.

The expression "detecting a signal based on light emitted from the label" means either direct or indirect detection of the light emitted from the label.

It is desirable that the rate of change in the magnitude of the signal based on the light emitted from the label be acquired in correspondence with the flow rate by detecting the signal while gradually increasing the flow rate of the liquid specimen over the sensor portion after the labeled binding material is bonded to the immobilization layer, and the constant flow rate be determined on the basis of the rate of change in the magnitude of the signal based on the light emitted from the label.

It is preferable that a flow rate at which the rate of change in the magnitude of the signal is half of the rate of change at the beginning of the measurement be determined to be the constant flow rate. Further, it is more preferable that a flow rate at which the rate of change in the magnitude of the signal becomes zero be determined to be the constant flow rate.

Alternatively, a flow rate which is appropriate for the combination of the labeled binding material and the immobilization layer and is acquired in advance may be determined to be the constant flow rate.

The detection system according to the present invention is characterized in that comprising a channel type sensor chip, a pump, an optical-signal detection device, and a signal processing controller. In the channel type sensor chip, a sensor portion is arranged in a microchannel formed in a channel member, a liquid specimen is to flow through the microchannel, and the sensor portion includes an immobilization layer capable of being bonded to a labeled binding material containing an attached label which emits light when irradiated with excitation light. The pump controls a flow rate of a fluid over the sensor portion. The optical-signal detection device includes, an excitation-light irradiation optical system for irradiating the sensor portion with excitation light, and an optical detector for detecting a signal based on light emitted from the sensor portion. The signal processing controller is connected to the pump and the optical-signal detection device, and includes a flow-rate determining means and a control means. The flow-rate determining means determines a constant flow rate for the fluid over the sensor portion so that bonds between the labeled binding material and the immobilization layer are not broken and the signal can be detected with a greater magnitude when the fluid flows at the constant flow rate than when the fluid exists over the sensor portion at rest, and the control means controls the pump and the optical-signal detection device so that the fluid over the sensor portion flows at the constant flow rate and the optical-signal detection device detects the signal while the fluid over the sensor portion flows at the constant flow rate.

It is desirable that the control means controls the pump and the optical-signal detection device so as to gradually increase the flow rate of the liquid specimen over the sensor portion, to detect the signal during the increase in the flow rate, and to acquire, in correspondence with the flow rate, the rate of change in the magnitude of the signal based on the light emitted from the label, and the flow-rate determining means determine a constant flow rate on the basis of the rate of change in the magnitude of the signal. In this case, it is preferable that the flow-rate determining means determine a predetermined flow rate at which the rate of change in the magnitude of the signal is half of the rate of change at the beginning of the measurement, to be the constant flow rate. Further, it is more preferable that the flow-rate determining means determine a flow rate at which the rate of change in the magnitude of the signal becomes zero, to be the constant flow rate.

Alternatively, a flow rate which is appropriate for the combination of the labeled binding material and the immobilization layer and is acquired in advance and stored in a predetermined storage means may be determined to be the constant flow rate. In this case, the detection system may be provided with a table indicating a relationship between each of combinations of the labeled binding material and the immobilization layer and the flow rate appropriate for the combination, and the constant flow rate may be determined on the basis of the combination used in the measurement and the table.

The predetermined storage means may be arranged either inside or outside the signal processing controller. For example, in the case where the predetermined storage means is a chip information portion, which is arranged in such a position in the sensor chip that the chip information portion does not affect the signal detection, it is sufficient to provide an information reading means which reads the appropriate flow rate from the chip information portion.

It is desirable that the sensor chip have an inlet arranged in the channel on the upstream side of the sensor portion for injection of the liquid specimen into the channel and an air port for flowing downstream the liquid specimen injected from the inlet, and the pump utilizes the inlet and the air port for making the fluid over the sensor portion flow at a flow rate.

In the case where the immobilization layer arranged in the channel type sensor chip is a layer in which a first binding material capable of being specifically bonded to the target material is immobilized, and the labeled binding material contains a second binding material capable of being specifically bonded to the target material and capable of being specifically bonded to the first binding material through the target material, the detection system is preferable for performing sandwich ELISA.

On the other hand, in the case where the immobilization layer is a layer in which a first binding material capable of being specifically bonded to the target material is immobilized, and the labeled binding material contains a third binding material capable of being specifically bonded to the first binding material, and competes with the target material for specific bonding to the first binding material, the detection system is preferable for performing competitive ELISA.

Further, it is desirable that a metal layer be arranged on a wall surface of the sensor portion in the channel, and the immobilization layer be arranged on the metal layer. Alternatively, it is possible to arrange an optical waveguide layer on the metal layer, and the immobilization layer on the optical waveguide layer. It is desirable that the main component of the metal layer be at least one of or an alloy of two or more of Au, Ag, Cu, Al, Pt, Ni, and Ti. The "main component" is defined as a component the content of which is 90 weight percent or more. The optical waveguide layer may be realized by, for example, a film of an inorganic oxide such as $SiO_2$, $TiO_2$, or $HfO_2$ or an organic polymer such as polystyrene or PMMA.

In the detection method or the detection system according to the present invention, the labeled binding material is bonded to the top of the sensor portion, and thereafter a fluid is moved over the sensor portion at a constant flow rate, so that a laminar flow is realized over the sensor portion. Because the labeled binding material is inclined in the direction of the flow by the laminar flow, the labeled binding material can be brought closer to the surface of the sensor portion. Since the signal based on the light emitted from the label is detected under the condition that the labeled binding material is brought close to the surface of the sensor portion, it is possible to efficiently utilize the region of the surface of the sensor portion at which the evanescent field or the enhanced optical field is strong. Therefore, the presence or absence of and/or the quantity of the target material can be precisely detected.

BRIEF DESCRIPTION OF THE DRAWINGS

FIG. 8 is a plan view of another example of a sensor chip.

FIG. 9 is a plan view of an example of a design change in the sensor chip.

FIG. 10 is a plan view of an example of a design change in the sensor chip.

FIG. 11 is a diagram schematically illustrating an outline of a portion of a detection system according to a third embodiment of the present invention.

DESCRIPTION OF PREFERRED EMBODIMENTS

Figure 1:
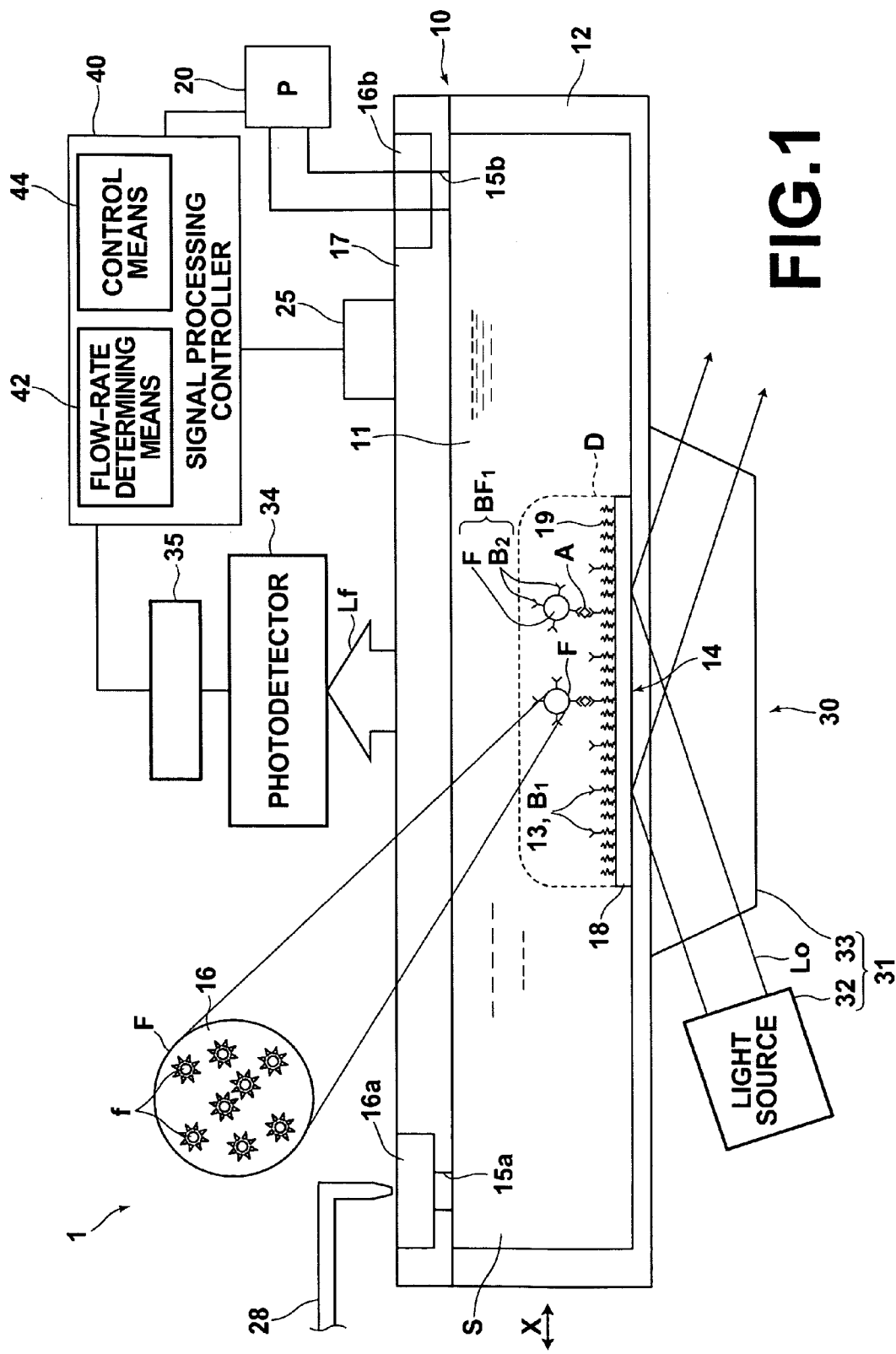
FIG. 1 is a diagram schematically illustrating an outline of a detection system according to a first embodiment of the present invention.

Preferred embodiments of the present invention are explained in detail below with reference to drawings. In the drawings, the dimensions of the illustrated elements are differentiated from the dimensions of the elements in the actual photoelectric conversion device for clarification.

<Detection System According to the First Embodiment>

Figure 2A:
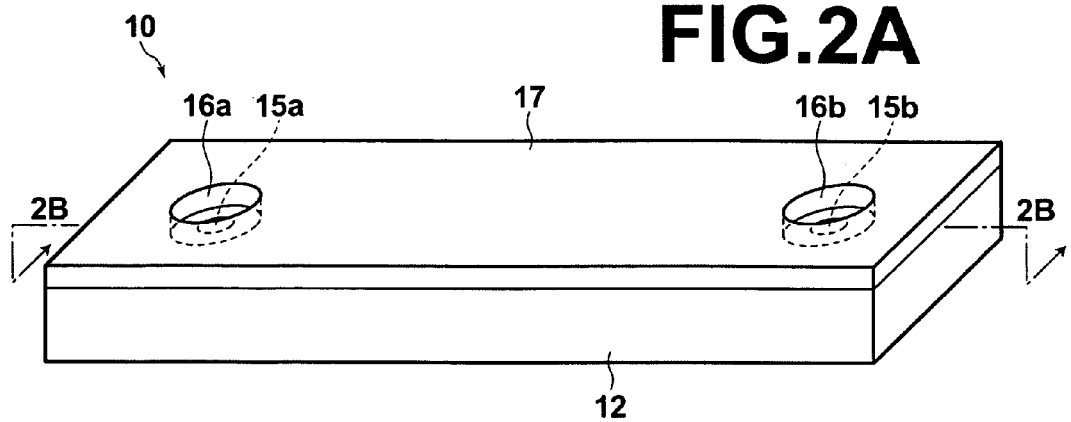
FIG. 2A is a perspective view of a channel type sensor chip used in the detection system according to the first embodiment of the present invention.
Figure 2B:
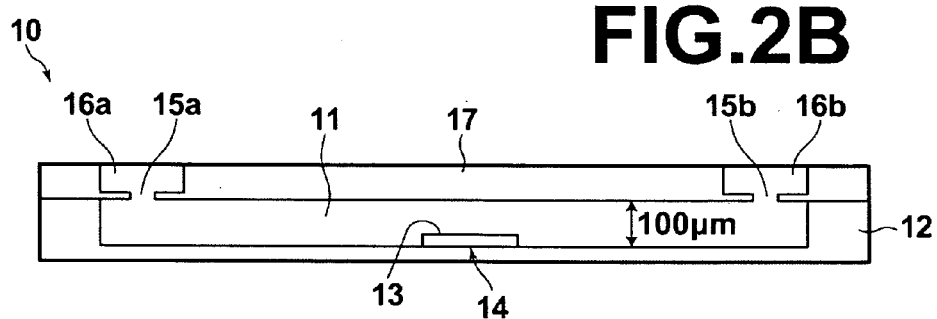
FIG. 2B is a side view of the channel type sensor chip used in the detection system according to the first embodiment of the present invention.
Figure 2C:
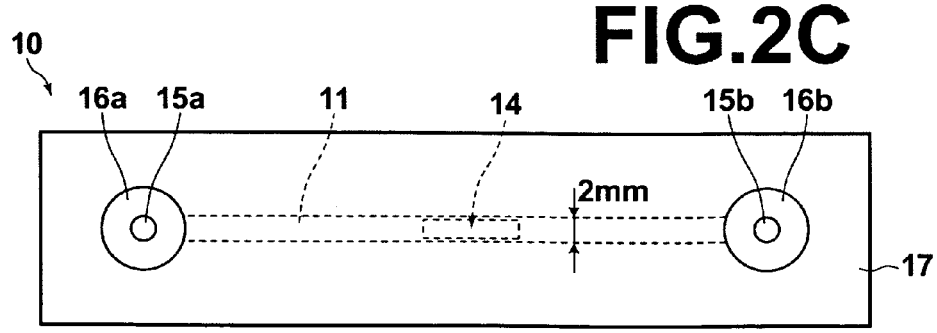
FIG. 2C is a plan view of the channel type sensor chip used in the detection system according to the first embodiment of the present invention.

FIG. 1 is a diagram schematically illustrating an outline of the detection system 1 according to the first embodiment of the present invention. FIGS. 2A to 2C are respectively perspective, side, and plan views of the structure of a sensor chip.

The detection system 1 comprises the channel type sensor chip 10, a pump 20, an optical-signal detection device 30, and a signal processing controller 40. The pump 20 controls the flow rate of a fluid in a channel in the channel type sensor chip 10. The signal processing controller 40 is connected to the pump 20 and the optical-signal detection device 30, and controls the pump 20 and the optical-signal detection device 30. According to the present embodiment, the detection system 1 further comprises a flow-rate measurement device 25 for measuring the flow rate of the fluid in the channel, and a pipette device for injecting a liquid specimen or a buffer solution into the channel (although only a pipette nozzle 28 is shown in FIG. 1).

A sensor portion 14 is arranged in the channel type sensor chip 10. In the sensor portion 14, an immobilization layer 13 is arranged in the channel 11 in a channel member 12, where a liquid specimen flows through the channel 11. The immobilization layer 13 is capable of being bonded to a labeled binding material $B_F$, and the labeled binding material $B_F$ is labeled with a label F which can emit light when irradiated with excitation light.

As illustrated in FIGS. 2A to 2C, the channel type sensor chip 10 is constructed by bonding an upper plate member 17 to the channel member 12 by ultrasonic welding. The upper plate member 17 have sumps 16a and 16b and openings 15a and 15b arranged at the bottoms of the sumps 16a and 16b. The channel member 12 and the upper plate member 17 are formed of transparent dielectric material such as polystyrene, and can be respectively formed by injection molding. For example, the channel has a width of approximately 2 millimeters and a depth of approximately 100 micrometers. In order to adjust the flow rate of the fluid in the channel, at least one opening (air port) is needed to be arranged on each of the upstream and downstream sides of the sensor portion 14 in the channel type sensor chip 10. According to the present embodiment, the opening 15a on the upstream side is used as an inlet for injecting the liquid specimen, and the opening 15b on the downstream side is connected to a pump.

In addition, according to the present embodiment, as illustrated in FIG. 1, a metal film 18 is arranged at the position nearest to the wall surface of the channel in the sensor portion 14 in the sensor chip 10, a self-organized film 19 is arranged on the metal film 18, and the immobilization layer 13 is arranged on the self-organized film 19. Specifically, the immobilization layer 13 is formed of a first binding material (e.g., a primary antibody) $B_1$ which can be specifically bonded to the target material (e.g., an antigen) A. In the explanations on the present embodiment, the sensor surface means the surface of the metal film. The metal film 18 can be formed by forming on the bottom surface of the channel a mask having an opening in a predetermined area and then performing a known evaporation technique. It is desirable that the thickness of the metal film 18 be appropriately determined according to the material of the metal film 18 and the wavelength of the excitation light so that the surface plasmons are strongly excited. For example, in the case where laser light having the center wavelength of 780 nanometers (nm) is used as the excitation light and a gold (Au) film is used as the metal film, the thickness of the metal film is preferably 50±20 nm, and more preferably 47±10 nm. In addition, the main component of the metal film is preferably at least one of or an alloy of two or more of Au, Ag, Cu, Al, Pt, Ni, and Ti.

The label F is a fluorescent material composed of a fluorescent molecule f and an optically transparent material 16 enclosing the fluorescent molecule f. In the case where the label F contains a plurality of fluorescent dye molecules f, the amount of the fluorescence is increased. Therefore, it is more preferable that the label F contain a plurality of fluorescent dye molecules f as illustrated in the partial magnification in FIG. 1. In the case where the fluorescent molecule f is enclosed in the optically transparent material 16 in such a manner that the fluorescent molecule f can be kept at a predetermined distance or more from the metal layer, it is possible to prevent metal quenching, which can occurs when the fluorescent dye molecule is located close to the metal film 18. Specifically, the material 16 may be, for example, polystyrene or $SiO_2$. However, the material 16 is not specifically limited as long as the material 16 can enclose a fluorescent dye molecule f, and transmit and externally emit the fluorescence emitted from the fluorescent dye molecule f.

The quenching, which can occur when the fluorescent dye molecule is located close to the metal layer, is associated with energy transfer to the metal, and the degree of the energy transfer to metal decreases in inverse proportion with the third power of the distance in the case where the metal is a plate with semi-infinite thickness, in inverse proportion with the fourth power of the distance in the case where the metal has a planar form with infinitely small thickness, and in inverse proportion with the sixth power of the distance in the case where the metal has the form of microparticles. Therefore, the distance between the metal film 18 and the fluorescent dye molecule f is preferably at least several nanometers, and more preferably 10 nanometers or greater.

The fluorescent material F can be produced, for example, in the following manner.

First, 0.1% solid in phosphate (polystyrene solution: pH7.0) is prepared by using polystyrene particles (Product #K1-050, Estapor, ø=500 nm, 10% solid, carboxyl group).

Subsequently, 1 mL of an ethyl acetate solution containing 3 mg of fluorescent dye (BODIPY-FL-SE, Product #D2184, MolecularProbes) is produced.

The polystyrene solution and the solution of the fluorescent dye are mixed, then impregnation is performed during evaporation. Thereafter, centrifugation (for 20 minutes at 15000 rpm and 4° C.) is performed (twice), and the supernatant is removed. When the above process is performed, the fluorescent material F in which polystyrene encloses the fluorescent dye can be produced. The diameter of grains in the fluorescent material F which is produced by impregnating polystyrene particles with a fluorescent dye through the above process is identical to the diameter of the polystyrene particles (which is 500 nm in the above example).

Although, in the present embodiment, the fluorescent material indicated above as an example of the label is composed of a fluorescent molecule f and an optically transparent material 16 enclosing the fluorescent molecule f, the label is not limited to the fluorescent material, may be another material (such as a quantum dot or a metal microparticle) which is optically responsive and emits some light (such as fluorescence or scattered light) when irradiated with excitation light.

The labeled binding material $B_F$ is a second binding material $B_2$ capable of being specifically bonded to a target material A and contains the label F which is attached. Although, in the present embodiment, sandwich ELISA is taken as an example, the labeled binding material is required only to be a binding material to which a label is attached and which is capable of being bonded to the immobilization layer 13 directly or through the target material A. In the case where competitive ELISA is performed, the labeled binding material is a third binding material $B_3$ which can be directly bonded to the immobilization layer 13 in competition with the target material A. In the case where the target material A is an antigen, the so-called primary antibody can be used as the first binding material $B_1$, and the so-called secondary antibody can be used as the labeled binding material.

The optical-signal detection device 30 comprises an excitation-light irradiation optical system 31 and a photodetector 34. The excitation-light irradiation optical system 31 irradiates the sensor portion 14 with the excitation light Lo, and the photodetector 34 detects a signal based on the light emitted from the sensor portion 14. The detection system according to the present embodiment is configured to cause surface plasmons at the surface of the metal film 18 in the channel type sensor chip 10 by injecting the excitation light Lo through the excitation-light irradiation optical system 31 onto the interface between the metal film 18 and the inner wall surface of the channel at a predetermined angle equal to or greater than the total reflection angle, and enhance the optical field of the evanescent field leaking from the surface of the metal film. In addition, the detection system according to the present embodiment is also configured to detect, by the photodetector from the upstream side along the channel, fluorescence emitted from the fluorescent material in the enhanced electric field. The excitation-light irradiation optical system 31 comprises a light source 32 and a prism 33. The light source 32 emits the excitation light Lo, and is realized by a semiconductor laser (LD) or the like. The prism 33 is arranged under the sensor portion of the sensor chip, and guides the excitation light Lo so that the excitation light Lo is totally reflected at the interface between the inner wall surface of the channel and the metal film 18. The prism 33 is arranged in contact with the channel member 12 through a refractive-index matching oil. The light source 32 is arranged so that the excitation light Lo is injected from a face of the prism 33 onto the inner wall surface of the channel in the sensor chip 10 at a specific angle which is equal to or greater than the total reflection angle and at which surface plasmon resonance occurs in the metal film. Further, a light guide member may be arranged between the light source 32 and the prism 33 when necessary. Furthermore, the prism 33 and a channel member 12 may be integrally formed. In order to cause the surface plasmons, the excitation light Lo injected onto the interface is p polarized.

Although, in the present embodiment, the excitation light Lo is assumed to be parallel light injected onto the interface at the predetermined angle θ, the excitation light Lo may be a fan beam (focused light) having a spread Δθ around the center angle θ. In the case where the fan beam is used, the excitation light Lo is injected onto the interface at the incident angles corresponding to the range from θ−Δθ/2 to θ+Δθ/2. Therefore, even when the refractive index of the medium over the metal film is changed according to whether or not the specimen is supplied to the region over the metal film and resultantly the resonance angle at which surface plasmons are produced is changed, it is possible to cope with the change in the resonance angle without adjusting the incident angle. In addition, it is more preferable that the fan beam have a flat distribution in which the intensity variations with the incident angle are small.

A CCD, PD (photodiode), photomultiplier, c-MOS, or the like can be used as the photodetector 34. It is desirable that a wavelength selection filter be arranged in front of the light receiving face of the photodetector 34, when necessary, in order to enable detection of only the desired optical signal (the fluorescence in this example).

The signal processing controller 40 comprises a flow-rate determining means 42 and a control means 44. The flow-rate determining means 42 determines a constant flow rate for the fluid over the sensor portion 14 so that bonds between the labeled binding material $B_F$ and the immobilization layer 13 are not broken and the signal can be detected with a greater magnitude when the fluid flows at the constant flow rate than when the fluid exists over the sensor portion 14 at rest. The control means 44 controls the pump 20 and the optical-signal detection device 30 so that the fluid over the sensor portion 14 flows at the constant flow rate and the optical-signal detection device 30 detects the signal while the fluid over the sensor portion 14 flows at the constant flow rate. Specifically, the signal processing controller 40 can be realized by a personal computer or the like. The signal from the optical-signal detection device 30 is amplified by an amplifier 35, and is then inputted into the signal processing controller 40.

According to the present embodiment, in order to determine the flow rate on the sensor portion 14 which is appropriate for signal measurement, the control means 44 in the signal processing controller 40 controls the pump 20 and the optical-signal detection device 30 so as to acquire the rate of change in the magnitude of the signal in correspondence with the flow rate by detecting the signal while gradually increasing the flow rate of the fluid over the sensor portion, and the flow-rate determining means 42 in the signal processing controller 40 determines the constant flow rate on the basis of the rate of change in the magnitude of the signal. The flow-rate determining means 42 may be configured so that a predetermined flow rate at which the rate of change in the magnitude of the signal is half of the rate of change at the beginning of the measurement is determined to be the constant flow rate. Alternatively, the flow-rate determining means 42 may be configured so that a flow rate at which the rate of change in the magnitude of the signal becomes zero is determined to be the constant flow rate.

The flow-rate measurement device 25 measures the flow rate of the fluid in the channel 11, is connected to the signal processing controller 40, and outputs the monitored flow rate to the signal processing controller 40. Since the flow rate in the channel can also be acquired from the output (suction force) of the suction pump, the flow rate meter is not necessarily provided. However, it is desirable that the flow rate meter be provided for precise measurement. Specifically, known measuring devices such as laser flow rate meters and ultrasonic flow rate meters can be used as the flow rate meter.

<Detection Method According to the First Embodiment>

In the detection method according to the first embodiment of the present invention using the above detection system 1, the labeled binding material in an amount corresponding to the quantity of a target material is bonded to the immobilization layer when the aforementioned channel type sensor chip 10 is used and the liquid specimen S is controlled to flow in the channel 11. Thereafter, the signal based on the light emitted from the label in the enhanced optical field which is produced on the surface of the sensor portion by irradiation of the sensor portion 14 with the excitation light is detected for detecting the quantity of the target material. The detection method according to the present embodiment is characterized in that, in order to detect the quantity of the target material, the signal is detected while the liquid specimen flows at the constant flow rate at which bonds between the labeled binding material and the immobilization layer are not broken and the signal can be detected with a greater magnitude than when the liquid specimen exists over the sensor portion at rest. According to the present embodiment, signal detection is performed after the flow rate appropriate for the signal detection is determined to be the constant flow rate.

In the flow of the fluid in the microscale channel arranged in the channel type sensor chip illustrated in FIGS. 1, 2A, 2B, and 2C or in the lab-on-a-chip (Laboratory on a Chip) device or the μ-TAS (Micro Total Analysis System), no turbulent flow occurs and the laminar flow is dominant in the case where an analyte of biological origin (such as blood or urine) is handled, since the analyte of biological origin has such a small Reynold number (Re) that Re<200. In the lab-on-a-chip device or the μ-TAS, laboratory processes such as electrophoresis, chemical reaction, cell culture, and separation and detection are integrated. The lab-on-a-chip device or the μ-TAS can also be used as the channel type sensor chip in the detection method and the detection system according to the present invention.

Figure 3:
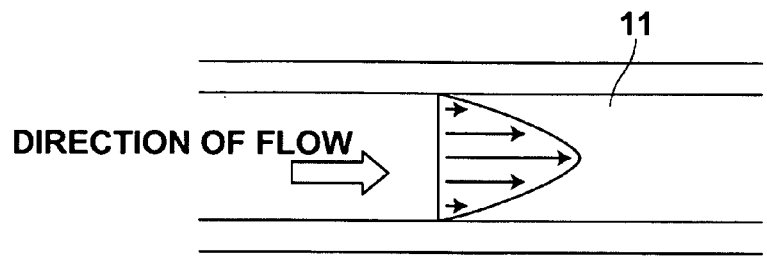
FIG. 3 is a diagram illustrating a distribution of the flow rate in a channel (laminar flow).

The laminar flow is a flow having streamlines parallel to the wall surface of the microchannel, the greatest flow rate at the central portion of the channel, and small flow rates in the vicinity of the wall surface of the channel due to the friction force, as illustrated in FIG. 3. Since the laminar flow has the distribution of the flow rate in the channel as indicated in FIG. 3, the labeling material is inclined due to the shear stress T. Resultantly, the distance between the labeling material and the sensor surface is reduced, so that the signal is enhanced. The shear stress T is expressed by the formula, $$T=\mu \cdot dv(z)/dz,$$

where the z direction is the direction of the normal of the sensor surface, v(z) is the flow rate along the flow direction in the channel, and μ is the coefficient of viscosity. The above formula indicates that the shear stress is great in the vicinity of the wall surface of the channel since generally the flow rate greatly varies with the distance from the wall surface in the vicinity of the wall surface of the channel.

Figure 4:
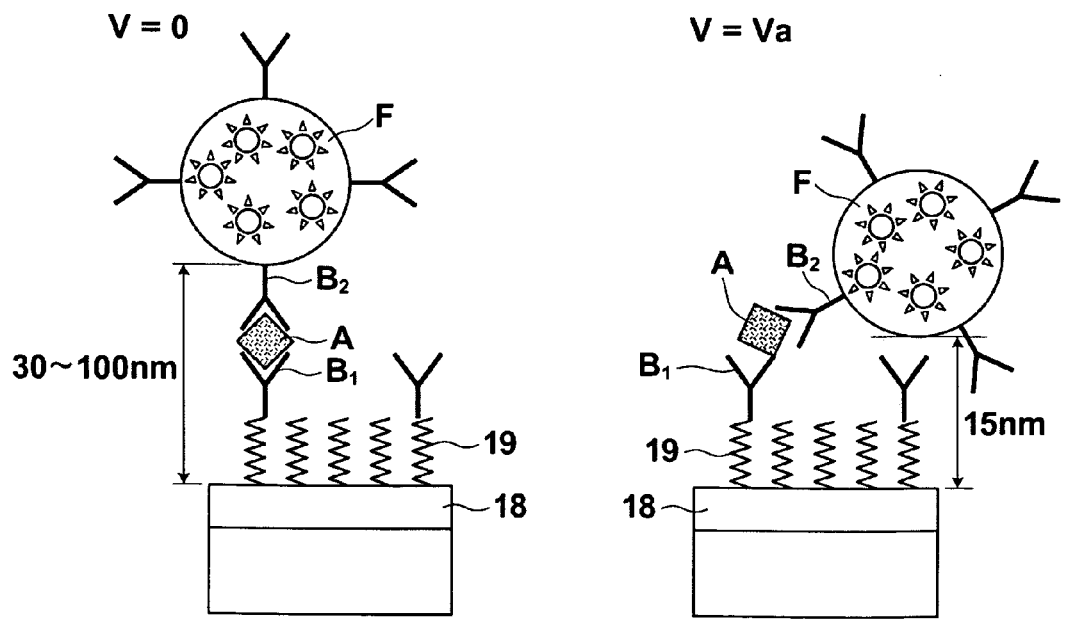
FIG. 4 is a schematic diagram illustrating states of bonding of an immobilization layer and a labeled binding material in a stationary fluid and in a laminar flow.

FIGS. 4A and 4B schematically indicates the states of the labeled binding material when the fluid is at rest (v=0), and when the fluid moves at a constant flow rate (v=$v_a$). In FIGS. 4A and 4B, it is assumed that a self-organized film having the thickness of 3 nanometers is arranged on the sensor surface, and an immobilization layer of a primary antibody $B_1$ (having the length of 10 to 50 nanometers) which can be specifically bonded to the target material A is arranged on the self-organized film. Further, it is assumed that the labeled binding material $B_F$ contains a labeling material F and a secondary antibody $B_2$ which can be specifically bonded to the target material A, and the labeling material F is a fluorescent material in which a fluorescent molecule f enclosed by a material which transmits the fluorescence emitted from the fluorescent molecule f.

In the case where the fluid is at rest, the labeled binding material is bonded to the immobilization layer and is also floating in the stationary fluid. Although the distance between the labeled binding material and the surface of the sensor portion depends on the labeled binding material and the size of the immobilization layer, the distance is approximately 30 to 100 nanometers in the case where a structure in which an antigen as the target material is sandwiched by two antibodies is formed as illustrated in FIGS. 4A and 4B. On the other hand, in the case where the fluid moves at a constant flow rate, the labeled binding material, which is bonded to the immobilization layer, is inclined due to the shear stress in the laminar flow, so that the distance between the labeling material and the immobilization layer can be reduced to approximately 15 millimeters. At this time, the distance from the sensor surface to the labeling material is assumed to be the minimum distance from the sensor surface to the surface of the labeling material.

Figure 5:
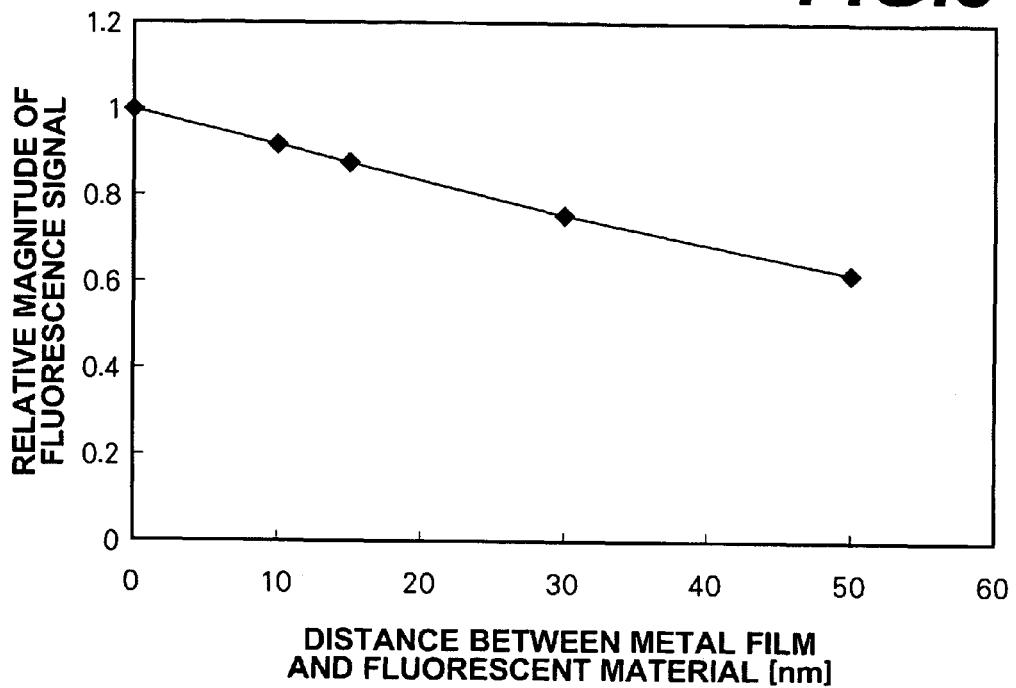
FIG. 5 is a diagram indicating a relationship between the relative magnitude of the signal and the distance between a metal film and a fluorescent material.

FIG. 5 is a diagram indicating a relationship between the relative magnitude of the signal and the distance between the fluorescent material and the sensor surface in the case where the fluorescent material as illustrated in FIGS. 4A and 4B is used as the labeling material. FIG. 5 indicates the calculation values obtained by a multilayer approximated simulation, which is performed for a system in which a solvent (water) exists over a sensor constituted by a prism (of polymethyl methacrylate (PMMA) resin) and a gold film having the thickness of 50 nanometers and being formed on the prism, under the condition that excitation light (having the laser wavelength of 656 nanometers) is injected onto the interface between the prism and the gold film at the incident angle of 72.5 degrees, and a fluorescent material in the form of spheres with the diameter of 310 nanometers is used as the label. In FIG. 5, the magnitude of the fluorescence signal at the zero distance (at which the fluorescent material is in contact with the sensor surface) is normalized to one.

As mentioned before, the fluorescent beads after formation of the sandwiched structure are approximately 30 nanometers or more distant from the sensor surface in the stationary fluid. As indicated in FIG. 5, the relative magnitude of the fluorescent signal is 0.75 or smaller in the stationary fluid, and can be improved to approximately 0.85 by reducing the distance from the fluorescent beads to the sensor surface to 15 nanometers.

As explained above, when a laminar flow is produced over the sensor portion, the shear stress is exerted on the labeling material bonded to the immobilization layer, so that the labeling material can be brought close to the surface of the sensor portion. Thus, signal detection with superior S/N and stability becomes possible.

Although the simulation is performed as explained above by using a fluorescent material, even in the case where a fluorescent molecule, a quantum dot, a metal microparticle, or the like is used as the label, the label is also affected by shear stress caused by the laminar flow, the effect of bringing the label closer to the sensor surface in the laminar flow than in the stationary fluid can also be achieved.

Figure 6:
FIG. 6 is a diagram indicating a relationship between the flow rate and the magnitude of the fluorescence.

FIG. 6 is a diagram roughly indicating a relationship between the flow rate and the magnitude of the fluorescence in the case where the flow rate over the sensor portion is gradually increased.

In the system in which the label (fluorescent material) is most distant from the sensor surface in the stationary fluid, more shear stress is exerted on the fluorescent material as the flow rate increases, so that the distance between the fluorescent material and the sensor surface is reduced, and therefore the amount of the fluorescence increases as indicated in FIG. 6. When the flow rate is further increased, the shear stress increases, so that the amount of the fluorescence further increases. However, when the flow rate becomes too great, the shear stress causes a phenomenon in which a specific bond in the sandwiched complex is broken and the fluorescent material comes off. At this time, the amount of the fluorescence greatly damps. Therefore, in practice, the flow rate should be such as to maximize the amount of the fluorescence (the magnitude of the signal) without making the fluorescent material come off. The manner of determining an appropriate flow rate will be explained later.

A sequence of steps in the detection method according to the present embodiment is explained below. In the explanations, a case in which an antigen A is detected as the target material contained in the biological specimen S such as urine or blood is taken as an example.

In the sensor chip 10 used in the present embodiment, a fluorescence-labeled binding material (labeled secondary antibody) $B_F$ is absorbed by and held in a portion of the channel 11 on the upstream side of the sensor chip 14 in advance, where the fluorescence-labeled binding material $B_F$ is composed of the fluorescent label F and the secondary antibody $B_2$, which is the second binding material capable of being specifically bonded to the antigen A.

1) First, the biological specimen S is injected by the pipette device 28 from the inlet 15a of the microchannel, and introduced into the microchannel 11 by suction in the suction pump 20 connected to the air port 15b.

2) The specimen introduced into the channel 11 is mixed with the labeled secondary antibody $B_F$ absorbed by and held in the channel, and the antigen A is bound by the secondary antibody $B_2$ in the labeled secondary antibody $B_F$. Further, the antigen A bonded to the secondary antibody $B_2$ is bonded to the first binding material $B_1$ being immobilized onto the sensor portion 14 and forming the immobilization layer 13. Thus, the so-called sandwich in which the antigen A is sandwiched by the first binding material $B_1$ and the second binding material $B_2$ (the labeled secondary antibody $B_F$) is formed.

3) A flow rate appropriate for measurement of the optical signal is determined. While the control means 44 controls the pump 20 so as to change the flow rate, and an optical signal is acquired from the photodetector 34 while the flow rate is changed. Then, the rate of change in the magnitude of the optical signal is obtained from the value of the flow rate obtained from the flow-rate measurement device 25 and the magnitude of the optical signal obtained from the photodetector 34, the flow-rate determining means 42 determines the flow rate $v_a$ at which the rate of change in the magnitude of the optical signal is approximately zero, to be the flow rate at which the optical signal is to be detected, and the control means 44 fixes the flow rate by controlling the pump.

Details of the sequence are as follows.

3a) Monitoring of variations in the magnitude of the optical signal with the variations in the flow rate is started. Specifically, the enhanced optical signal is produced on the sensor surface by irradiation with the excitation light, and detection, by the photodetector, of the magnitude I of the optical signal emitted from the labeling material is started. Then, the flow rate v of the fluid in the channel is gradually increased by pump manipulation. Thus, the rate of change in the magnitude of the optical signal in correspondence with the flow rate is acquired by detecting the optical signal while gradually increasing the flow rate of the fluid over the sensor portion. At this time, a precise value of the flow rate is detected by a flow rate meter. The fluid in the channel 11 may be a remainder of the specimen after the bonding reaction, or a buffer solution which is injected into the channel 11 by the pipette device when necessary.

3b) As indicated in FIG. 6, as the flow rate increases, the magnitude I of the optical signal increases, is then saturated, and is thereafter decreases. Therefore, the maximum magnitude I of the optical signal can be detected when the rate of change (dI/dv) in the magnitude of the optical signal becomes approximately zero after decrease in the rate of change (dI/dv). Thus, the pump manipulation is stopped at the flow rate $v_a$ at which the rate of change in the magnitude of the optical signal becomes approximately zero, and the flow rate $v_a$ is determined to be the flow rate at which the optical signal is to be detected for detection of the target material.

4) The magnitude of the optical signal emitted from the sensor portion is detected and acquired while the flow rate v of the fluid in the channel is maintained and fixed at the constant flow rate $v_a$ by the suction operation of the pump 20.

Although the time at which the rate of change in the magnitude of the optical signal is approximately zero is the most preferable timing for acquisition of the optical signal, the present invention is not limited to the most preferable timing as long as bonds between the labeled binding material and the immobilization layer are not broken and the signal can be detected with a greater magnitude than when the liquid specimen exists over the sensor portion at rest. For example, the timing for acquisition of the optical signal may be the time at which the rate of change in the magnitude of the optical signal is half of the rate of change at the beginning of the measurement (i.e., $dI/dv = \frac{1}{2} \times dI(0)/dv(0)$), or a predetermined flow rate at which the rate of change in the magnitude of the optical signal is greater than zero and less than half of the rate of change at the beginning of the measurement.

As explained above, when the fluorescence is detected under the condition that the fluorescent material is brought close to the sensor portion by moving the fluid over the sensor portion at a constant flow rate, the enhanced optical field can be effectively utilized, and the signal with superior S/N can be obtained, so that the reliability of the test can be improved.

<Detection System According to the Second Embodiment>

Figure 7:
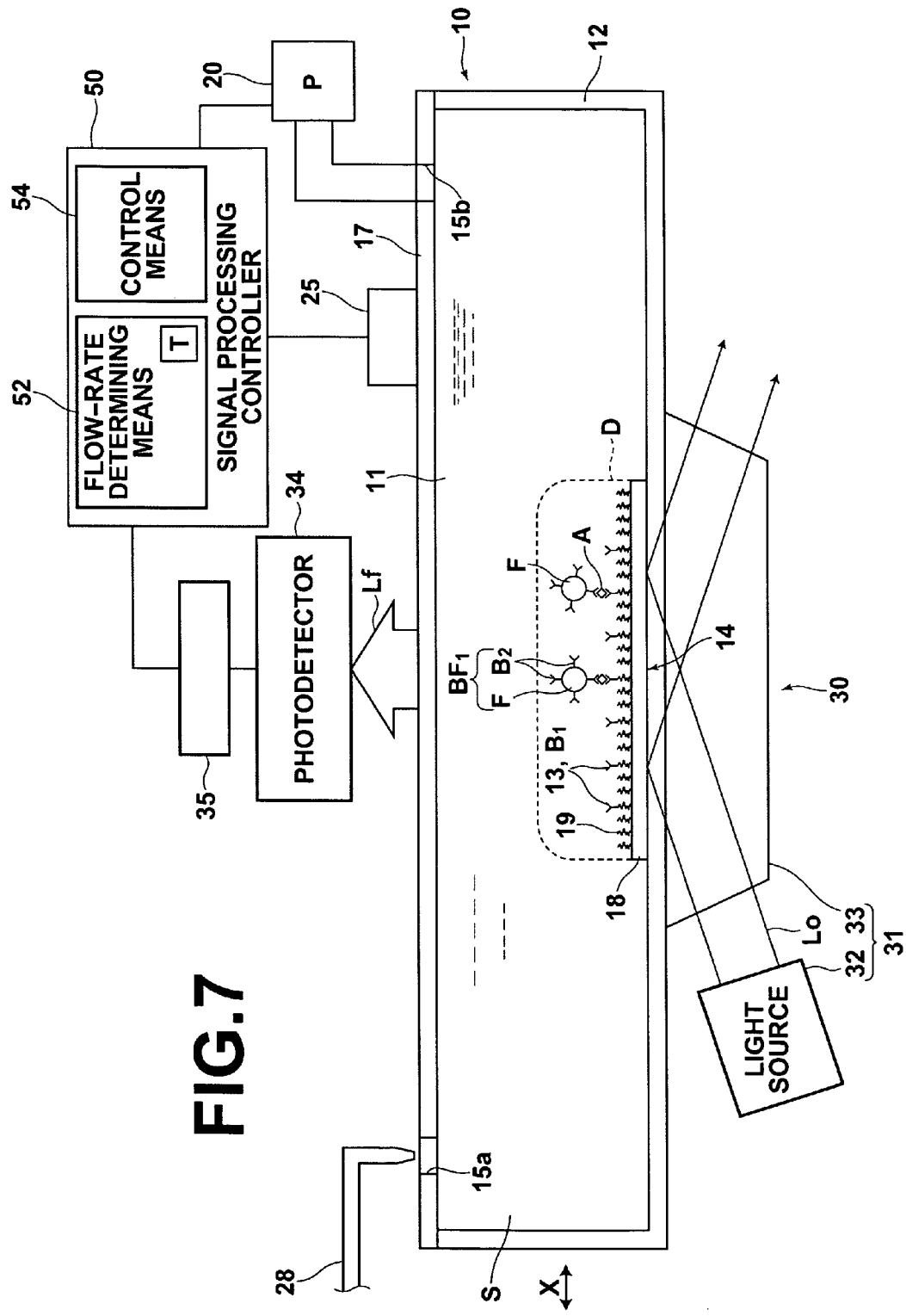
FIG. 7 is a diagram schematically illustrating an outline of a detection system according to a second embodiment of the present invention.
Figure 12:
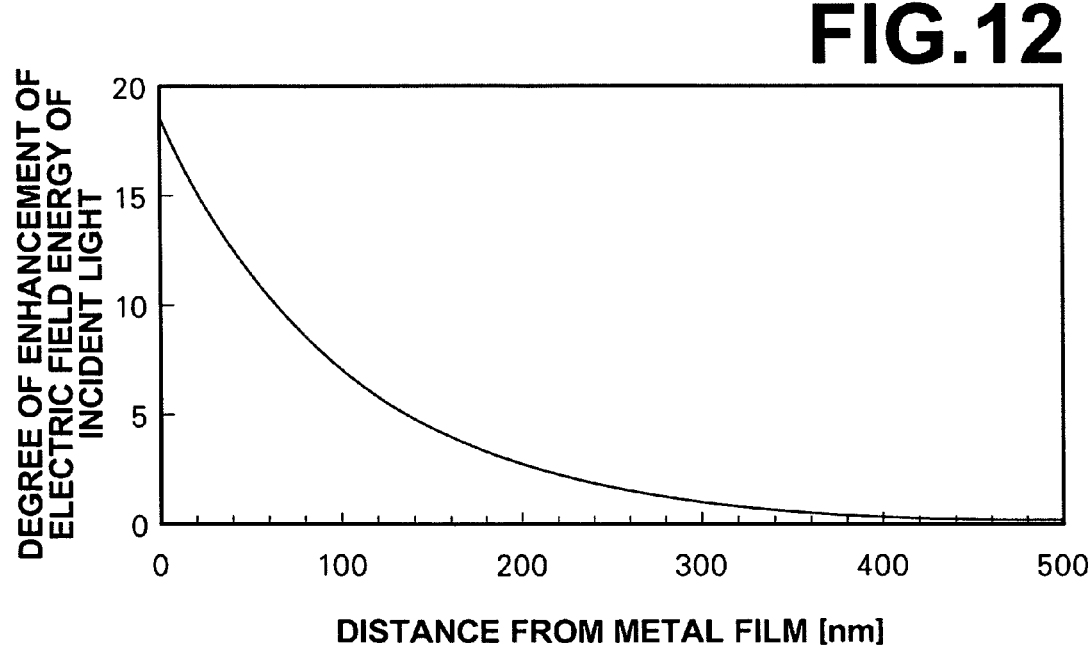
FIG. 12 is a diagram indicating a dependence of the degree of enhancement of the electric field energy of the incident light upon the distance from the metal film.

The detection system and the detection method according to the second embodiment are explained with reference to FIG. 7. FIG. 7 is a diagram schematically illustrating an outline of the detection system 2 according to the second embodiment of the present invention. In FIG. 7, elements and constituents identical to the corresponding elements in the first embodiment are indicated by the same reference numbers as the first embodiment, and descriptions of the identical elements are not repeated in the following explanations. In addition, the illustration of the sumps is omitted.

The detection system illustrated in FIG. 7 is different from the system according to the first embodiment in the construction of a signal processing controller 50. Specifically, in the signal processing controller 50 in the present embodiment, a storage means in a flow-rate determination means 52 comprises a table T, which indicates the correspondences between a plurality of combinations of the labeled binding material and the immobilization layer and the constant flow rates respectively appropriate for the plurality of combinations. In addition, the signal processing controller 50 determines, on the basis of the table T, a constant flow rate corresponding to the combination used in the detection.

<Detection Method According to the Second Embodiment>

The detection method according to the second embodiment is different from the first embodiment in the process for determining a constant flow rate appropriate for performing signal detection.

As mentioned before, when the flow rate is increased in the state in which the labeled binding material $B_F$ is bonded to the immobilization layer 13 on the sensor portion, and the shear stress produced by the laminar flow exceeds the bonding force between the immobilization layer and the binding material, the binding material begins to come off. The coming off depends on the strength of the specific bonding, which is determined by the types of the immobilization layer (the type of the first binding material) and the labeled binding material (e.g., the types of the antigen and the antibody). Therefore, the flow rate appropriate for the combination of the immobilization layer and the labeled binding material (e.g., the combination of the antigen and the antibody) which is subject to the test is experimentally obtained and stored in advance in some form such as the chip information. Thereafter, in actual testing, detection of the optical signal is performed at the flow rate appropriate for the combination used in the testing.

In the case of sandwich ELISA, the labeled binding material (the second binding material) is bonded to the immobilization layer (the first binding material) through the target material (antigen). Therefore, a flow rate appropriate for each combination of the first binding material, the antigen, and the second binding material is obtained in advance. In the case of competitive ELISA, the labeled binding material (the third binding material) is bonded directly to the immobilization layer (the first binding material). Therefore, a flow rate appropriate for each combination of the pair of the first binding material and the third binding material and the pair of the first binding material and the antigen is obtained in advance.

In a preferable manner of experimentally obtaining the flow rate, similar to the step 3) in the aforementioned sequence in the first embodiment, the variations in the rate of change in the magnitude of the optical signal are monitored by measuring the magnitude of the fluorescence signal and the rate of change in the magnitude of the optical signal while increasing the flow rate. Then, a predetermined flow rate at which the rate of change in the magnitude of the optical signal is greater than zero and less than half of the rate of change at the beginning of the measurement (i.e., $dI/dv=½×dI(0)/dv$ (0)) is determined to be the appropriate flow rate, and stored in advance in correspondence with the combination of the immobilization layer and the binding material.

In the detection system 2 according to the present embodiment, the storage means in the flow-rate determination means 52 comprises the table T, which indicates the correspondences between the plurality of combinations of the labeled binding material and the immobilization layer and the constant flow rates respectively appropriate for the plurality of combinations. The detection system 2 is configured to determine, by reference to the table T, an appropriate flow rate corresponding to the actual object subject to detection.

Hereinbelow, a sequence of operations in the detection method according to the present embodiment is explained. The step in which the specimen S is injected into the microchannel 11 and the sandwich of the antigen by the first binding material (the primary antibody) and the second binding material (the secondary antibody) is formed over the sensor portion is performed in a similar manner to the step 1) and 2) in the first embodiment.

3') The flow rate appropriate for measurement of the optical signal is determined. The flow-rate determining means 52 in the signal processing controller 50 determines a constant flow rate in correspondence with a combination used in detection by reference to the table T, which indicates the correspondences between the plurality of combinations of the labeled binding material and the immobilization layer and the constant flow rates respectively appropriate for the plurality of combinations.

4') The magnitude of the optical signal emitted from the sensor portion is detected and acquired by the photodetector under the condition that the flow rate v of the fluid in the channel is maintained and fixed at the constant flow rate by the suction operation of the pump 20.

According to the present embodiment, similar to the first embodiment, the fluorescence is detected under the condition that the fluorescent material is brought close to the sensor portion by moving the fluid over the sensor portion at the constant flow rate. Therefore, it is possible to effectively utilize the enhanced optical field, obtain the signal with superior S/N, and improve the reliability of the test.

Although the table indicating the correspondences between the combinations of the labeled binding material and the immobilization layer and the constant flow rates respectively appropriate for the combinations is provided in the flow-rate determination means 52 in the embodiment explained above, the combinations of the labeled binding material and the immobilization layer and the constant flow rates respectively appropriate for the combinations may be stored in a storage means having another form. For example, as illustrated in FIG. 8, a chip information portion 60 may be arranged at such a position on the upper surface of a channel type sensor chip 10' that the chip information portion 60 does not affect the signal measurement, where the chip information portion 60 stores information on one or more flow rates appropriate for one or more combinations of the immobilization layer and one or more binding materials capable of being bonded to the immobilization layer. In addition, an information reading means which reads an appropriate flow rate from the chip information portion 60 may be arranged in the detection system so that, when measurement is performed by using the channel type sensor chip 10', the information reading means can read an appropriate flow rate from the chip information portion 60, and the flow-rate determination means can determine the appropriate flow rate to be the constant flow rate.

In the chip information portion 60, information may be recorded by a bar code or the like, or an IC chip may be arranged. In this case, it is sufficient to arrange as the information reading means a bar code reader or an IC reader according to the form of the information recording in the chip information portion 60.

In the channel type sensor chip 10 according to each of the above embodiments, the air ports 15a and 15b respectively arranged on the upstream and downstream sides of the sensor portion enable adjustment of the flow rate in the channel. Although the configuration for moving the fluid by suction operation of the pump 20 connected to the air port 15b is explained before, alternatively, it is possible to connect a pump to the inlet 15a and move the fluid by extrusion.

Examples of design variations of the channel type sensor chip 10 are explained below. FIGS. 9 and 10 are plan views of sensor chips 10A and 10B as the examples of design variations.

In the sensor chip 10A illustrated in FIG. 9, an air port 71 is arranged in the channel between the inlet 15a and the sensor portion 14. When an extrusion pump is connected to the air port 71, and the fluid can be moved to the downstream side by extrusion.

In the sensor chip 10B illustrated in FIG. 10, a branch 72 from the channel is arranged between the inlet 15a and the sensor portion 14, and an air port 73 is arranged at the end of the branch 72. When an extrusion pump is connected to the air port 73, the fluid can be moved toward the downstream side by extrusion. In the channel having a branch as in the channel type sensor chip 10B, in order to prevent movement of the fluid toward the inlet 15a due to the extrusion by the pump, it is necessary to keep a sufficient amount of buffer solution in the sump, close the inlet 15a with a plug, or arrange a check valve on the upstream side of the branch point.

Further, it is possible to use a sensor chip in which four or more air ports are arranged in the channel, or a sensor chip in which a pump is arranged at each of two or more air ports. The pump is not limited to a pressure pump (which applies pressure so as to cause a flow) as long as the pump have a general function of controlling fluid convey and can be used in a microchannel. For example, the pump may be an electroosmotic pump.

In the explained embodiments, a fluorescent material is used as the label, an enhanced optical field is produced on the surface of the sensor portion by surface plasmons, and the detected optical signal is based on the light emitted by excitation of the fluorescent material in the enhanced optical field. However, the manner of enhancing the optical field is not limited to the surface plasmon resonance, and may be localized plasmon resonance or excitation of the optical waveguide mode. In addition, the fluorescence emitted from the fluorescent material may be detected either directly or indirectly. Further, the label is not limited to the fluorescent material, and may be a fluorescent dye molecule or a quantum dot. In this case, the fluorescence emitted from the fluorescent dye molecule or the quantum dot may be detected either directly or indirectly. Furthermore, in the case where the metal microparticle is used as the label, it is possible to detect the excitation light scattered by the metal microparticle. Moreover, in the case where the fluorescence signal is detected in the evanescent-excited fluorescence technique in which the enhanced optical field is not used, the phenomenon in which the evanescent field rapidly damps with the distance from the sensor surface similarly occurs. Therefore, it is possible to similarly achieve the effect of enhancing the magnitude of the optical signal, and improve S/N.

The optical field enhanced by the localized plasmon resonance can be produced by arranging on a sensor portion a metal microstructure or a plurality of metal nanorods, instead of the metal film, where the metal microstructure has on a surface a projection-and-recess substructure with dimensions smaller than the wavelength of the excitation light Lo and produces the so-called localized plasmons when irradiated with the excitation light, and the plurality of metal nanorods have dimensions smaller than the wavelength of the excitation light Lo. In the case where the localized plasmons as above are produced, the excitation-light irradiation optical system can be configured for irradiation with the excitation light Lo as either transillumination or epi-illumination. Alternatively, the metal microstructures disclosed in Japanese Unexamined Patent Publication Nos. 2006-322067 and 2006-250924, which utilize microstructures obtained by anodization of metal bodies and have various forms, can be used as the above metal microstructure producing the localized plasmons when irradiated with the excitation light.

The optical field enhanced by the optical waveguide mode can be produced by arranging an optical waveguide layer on the metal film on the sensor portion, and a self-organized film and an immobilization layer on the optical waveguide layer.

<Third Embodiment>

A system and a method for indirectly detecting an optical signal emitted from the label are explained below with reference to FIG. 11. FIG. 11 is a diagram illustrating the construction of an essential portion, including a channel type sensor chip 10 and an optical-signal detection device 30', of the detection system 3 according to the third embodiment of the present invention. The optical-signal detection device 30' in the detection system 3 according to the present embodiment is different from the optical-signal detection device 30 in the detection system 1 according to the first embodiment in the arrangement of the photodetector 34. The detection system 3 is configured to produce the optical field D enhanced by the surface plasmon resonance, and the fluorescence excited by the enhanced optical field newly induces surface plasmons in the metal film 18. In addition, the detection system 3 is further configured to detect light emitted downward from the newly induced plasmons.

The light caused by the newly induced plasmons is detected by the optical-signal detection device 30', and the principle of the detection of the light caused by the newly induced plasmons is explained below.

The sensor portion 14 is irradiated with the excitation light Lo by injecting the excitation light Lo through the excitation-light irradiation optical system 31 onto the interface between the metal film 18 and the wall surface of the channel at a specific incident angle equal to or greater than the total reflection angle. At this time, an evanescent wave leaks into the specimen S on the metal film 18, and the evanescent wave excites surface plasmons in the metal film 18. Therefore, the optical field produced on the metal film by the injection of the excitation light (i.e., the electric field caused by the evanescent wave) is enhanced by the surface plasmons so as to form an optical-field enhancement region D over the metal film. Since the fluorescent material F in the optical-field enhancement region D is brought close to the surface of the metal film, the fluorescent material F (actually, the fluorescent dye molecule f in the fluorescent material) is excited, so that fluorescence, which is enhanced by the effect of the surface plasmons enhancing the optical field, is generated. The fluorescence generated over the metal film 18 newly induces surface plasmons in the metal film 18, and light Lp is emitted by the newly induced surface plasmons at a specific angle from the side of the channel type sensor chip 10 opposite to the surface on which the metal film is formed. The presence or absence and/or the amount of the target material bonded to the labeled binding material can be detected by detecting the light Lp by the photodetector 34.

Since the light Lp is generated when the fluorescence is coupled to the surface plasmons having a specific wave number in the metal film, the wave number of the surface plasmons coupled to the fluorescence is determined according to the wavelength of the fluorescence, and the outgoing angle of the emitted light Lp is determined according to the wave number. Since the wavelengths of the light Lp and the fluorescence are different, the surface plasmons excited by the fluorescence have a wave number different from the surface plasmons generated by the excitation light Lo, and the outgoing angle of the emitted light Lp is different from the incident angle of the excitation light Lo.

As explained above, even in the case where the fluorescence emitted from the label is indirectly detected, the enhanced optical field is utilized. Therefore, the S/N of the signal can be improved by bringing the label close to the surface of the sensor portion, so that the detection method and the detection system according to the present invention, in which the label is brought close to the surface of the sensor portion by utilizing the laminar flow, are effective.

The invention claimed is:

1. A detection system, comprising:
a channel type sensor chip in which a sensor portion is arranged in a microchannel formed in a channel member, where a liquid specimen is to flow through the microchannel, and the sensor portion includes an immobilization layer bonded to a labeled binding material comprising an attached label which emits light when irradiated with excitation light;

a pump which controls a flow rate of a fluid over said sensor portion;
an optical-signal detection device, including:
   an excitation-light irradiation optical system for irradiating said sensor portion with excitation light; and
   an optical detector for detecting a signal based on light emitted from said sensor portion; and
a signal processing controller being connected to said pump and said optical-signal detection device, wherein the signal processing controller comprises a program installed therein to control said pump and said optical-signal detection device, the program comprising instructions for:
   bonding the labeled binding material to the immobilization layer in an amount corresponding to a quantity of a target material contained in said liquid specimen, by causing the liquid specimen to flow through the microchannel;
   determining a constant flow rate for said fluid over said sensor portion so that bonds between the labeled binding material and the immobilization layer are not broken, and said signal can be detected with a greater magnitude when the fluid flows at the constant flow rate than when the fluid exists over the sensor portion at rest;
   flowing the fluid over the sensor portion at said constant flow rate; and
   detecting the quantity of the target material by detecting a signal based on light emitted from the attached label existing in an evanescent field or an enhanced optical field which is produced over a surface of the sensor portion when the sensor portion is irradiated with the excitation light while the fluid over said sensor portion flows at said constant flow rate.

2. A detection system according to claim 1, wherein said program further comprises instructions for:
   acquiring a rate of change in a magnitude of said signal in correspondence with the flow rate of the fluid over said sensor portion by detecting the signal while gradually increasing the flow rate; and
   determining said constant flow rate on a basis of the rate of change in the magnitude of the signal.

3. A detection system according to claim 2, wherein said program further comprises instructions for:
   determining a predetermined flow rate at which the rate of change in the magnitude of said signal is equal to or less than half of the rate of change when measurement is started to be said constant flow rate.

4. A detection system according to claim 2, wherein said program further comprises instructions for:
   determining a flow rate at which the rate of change in the magnitude of said signal is zero to be said constant flow rate.

5. A detection system according to claim 1, further comprising:
   predetermined storage means which stores a flow rate suited for a combination of the labeled binding material and the immobilization layer and is acquired and stored in the predetermined storage means in advance,
   wherein said program further comprises instructions for determining the flow rate suited for the combination of the labeled binding material and the immobilization layer stored in the predetermined storage means to be said constant flow rate for the combination of the labeled binding material and the immobilization layer.

6. A detection system according to claim 5, wherein said predetermined storage means is arranged in said signal processing controller.

7. A detection system according to claim 5, wherein said predetermined storage means comprises a chip information portion which is arranged in such a position that the chip information portion does not affect detection of said signal, and said detection system comprises information reading means which reads said flow rate appropriate for said combination.

8. A detection system according to claim 1, wherein said sensor chip comprises an inlet and an air port, the inlet is arranged in said microchannel on an upstream side of said sensor portion for injecting said liquid specimen into the channel, the air port is arranged in the channel on a downstream side of the sensor portion for flowing toward the downward side the liquid specimen injected from the inlet, and said pump makes the fluid over the sensor portion flow at a flow rate, by utilizing said inlet or said air port.

9. A detection system according to claim 1, wherein the labeled binding material is bonded to a top section of the sensor portion such that a laminar flow is realized over the sensor portion.

10. A detection system according to claim 9, wherein the labeled binding material is inclined in a direction of the laminar flow to reduce a distance between the labeled binding material and a surface of the sensor portion.

11. A detection system according to claim 9, wherein the labeled binding material is inclined in a direction of the laminar flow to reduce a distance between the labeled binding material and the immobilization layer.

* * * * *